(12) United States Patent
Esposti et al.

(10) Patent No.: US 12,194,288 B2
(45) Date of Patent: Jan. 14, 2025

(54) METHOD FOR DETERMINING ARTIFICIAL PUMP DYSFUNCTION

(71) Applicant: OSPEDALE SAN RAFFAELE S.R.L., Milan (IT)

(72) Inventors: Federico Esposti, Milan (IT); Filippo Consolo, Milan (IT); Federico Severine Pappalardo, Milan (IT)

(73) Assignee: OSPEDALE SAN RAFFAELE S.R.L., Milan (IT)

( * ) Notice: Subject to any disclaimer, the term of this patent is extended or adjusted under 35 U.S.C. 154(b) by 626 days.

(21) Appl. No.: 17/275,886

(22) PCT Filed: Sep. 13, 2019

(86) PCT No.: PCT/EP2019/074505
§ 371 (c)(1),
(2) Date: Mar. 12, 2021

(87) PCT Pub. No.: WO2020/053395
PCT Pub. Date: Mar. 19, 2020

(65) Prior Publication Data
US 2021/0252275 A1    Aug. 19, 2021

(30) Foreign Application Priority Data
Sep. 13, 2018   (EP) .................................... 18194294

(51) Int. Cl.
*A61M 60/148*   (2021.01)
*A61M 60/178*   (2021.01)
(Continued)

(52) U.S. Cl.
CPC ........ *A61M 60/515* (2021.01); *A61M 60/148* (2021.01); *A61M 60/178* (2021.01);
(Continued)

(58) Field of Classification Search
None
See application file for complete search history.

(56) References Cited

U.S. PATENT DOCUMENTS

2011/0032107 A1   2/2011  Sasaki
2011/0313238 A1*  12/2011 Reichenbach ...... A61M 60/216
                                                      600/16
(Continued)

FOREIGN PATENT DOCUMENTS

WO   2019/013794 A1   1/2019
WO   2019/147444 A1   8/2019

OTHER PUBLICATIONS

ISA/EP, "PCT International Search Report and Written Opinion", which was issued in connection with corresponding PCT application No. PCT/EP2019/074505, and mailed on Nov. 28, 2019 (13 pages).

*Primary Examiner* — Ankit D Tejani
(74) *Attorney, Agent, or Firm* — Lucas & Mercanti, LLP

(57) ABSTRACT

The present invention relates to a method for early detection of artificial pump dysfunction based on a time-frequency analysis of the pump motor power consumption (PRC). The method allows to prevent low output syndrome, cardiogenic shock, pump thrombus and/or cardiac arrest or death as well as to monitor the efficacy of a thrombolytic therapy and/or to optimize intensity and duration of a thrombolytic therapy.

19 Claims, 6 Drawing Sheets

Figure 1:
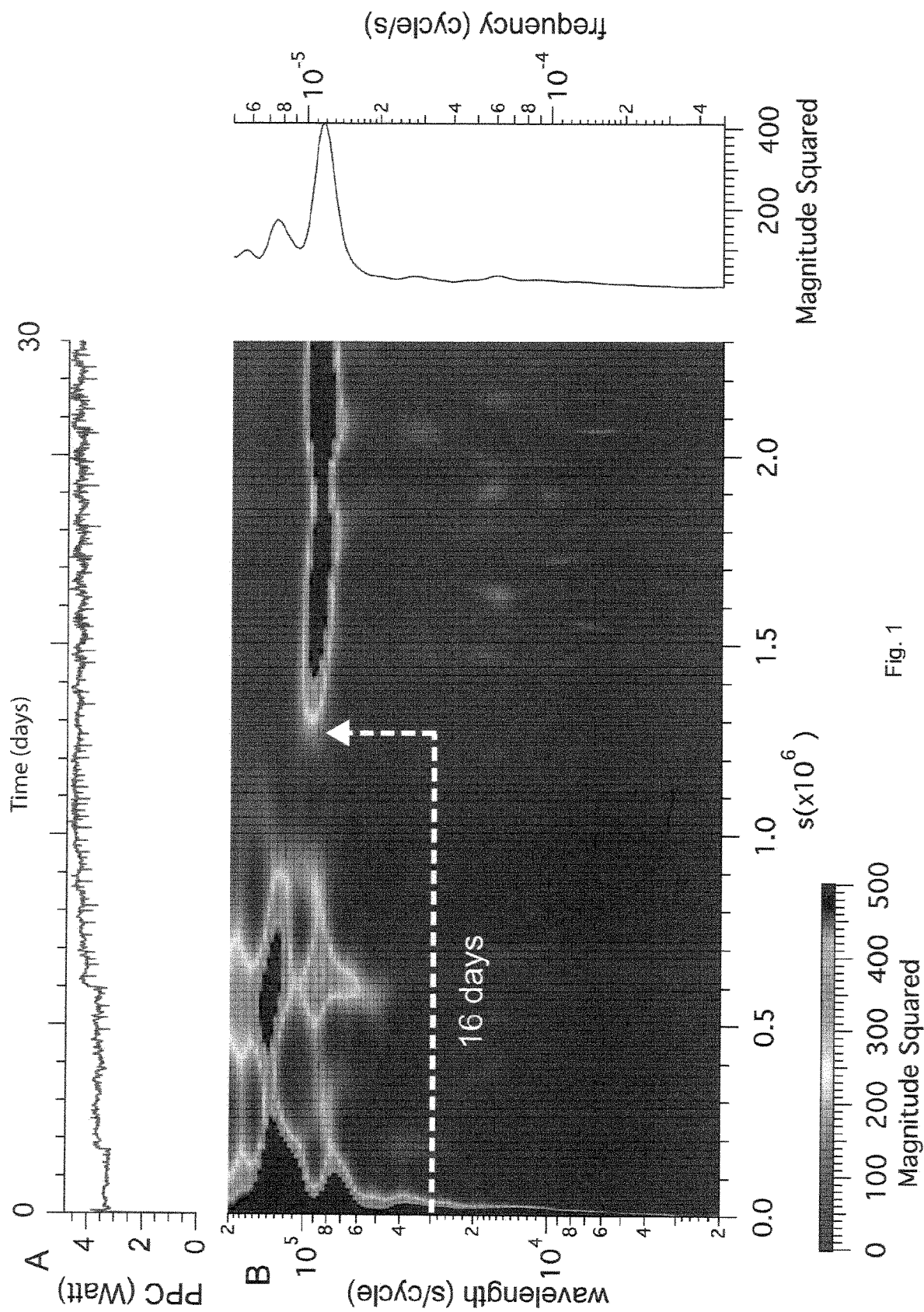

(51) Int. Cl.
  *A61M 60/216* (2021.01)
  *A61M 60/515* (2021.01)
  *A61M 60/538* (2021.01)

(52) U.S. Cl.
  CPC ........ *A61M 60/216* (2021.01); *A61M 60/538* (2021.01); *A61M 2205/18* (2013.01)

(56) References Cited

U.S. PATENT DOCUMENTS

2017/0119256 A1   5/2017  Demou et al.
2017/0209632 A1   7/2017  Pierce et al.
2017/0239418 A1*  8/2017  Levine ................. A61M 37/00

* cited by examiner

METHOD FOR DETERMINING ARTIFICIAL PUMP DYSFUNCTION

CROSS-REFERENCE TO RELATED APPLICATIONS

This application is a 371 of PCT/EP2019/074505, filed Sep. 13, 2019, which claims the benefit of European Patent Application No. 18194294.7, filed Sep. 13, 2018.

TECHNICAL FIELD

The present invention relates to a method for early detection of artificial pump dysfunction based on a time-frequency analysis of the pump motor power consumption (PPC). The method allows to prevent low output syndrome, cardiogenic shock, pump thrombus and/or cardiac arrest or death as well as to monitor the efficacy of a thrombolytic therapy and/or to optimize intensity and duration of a thrombolytic therapy.

BACKGROUND ART

Mechanical circulatory support with continuous-flow Left Ventricular Assist Devices (LVADs) is a viable therapy for the treatment of end-stage heart failure (1). LVAD support provides optimal hemodynamic recovery, improves functional capacity and quality of life, and increases survival (1-3). However, despite clinical efficacy, potential risks and complications associated with LVAD therapy exist, which severely affect long-term outcomes. In particular, pump thrombosis (PT) is a major and severe complication (4-6). PT is a multifaceted and complex phenomenon, where several elements, including patient- and device-specific characteristics, synergize with systemic factors to the development of the thrombotic event (7-9). PT can occur due to in-pump thrombus formation (i.e., build up) or ingestion of a mobilized thrombus from the inflow cannula or left-side heart chambers (10,11). In both situations, the result is impingement of the impeller from property rotating and associated severe pump operating dysfunction. If not promptly diagnosed and treated, PT may lead to low-output syndrome, cardiogenic shock or even pump stop and death. Treatment is based on intravenous anticoagulation and/or thrombolytic therapy (12). However, the success rate of medical therapy is highest at an early stage of PT and decreases dramatically in the case of late diagnosis (10). In case of treatment failure or severe cardiac insufficiency, emergency exchange of the pump remains the only therapeutic option. Data from the INTERMACS database reveal a significant drop in survival following pump exchange secondary to PT (13). Attendant costs for reoperation and patient management are also extremely high (14).

On clinical grounds, diagnosis of PT is based on the analysis of the pump log-files, as it is typically preceded by significant changes in pump motor power consumption (PPC) associated with modifications of the pump workload (15). Detection of symptoms of hemolysis (dark urine, elevations of lactate dehydrogenase and/or plasma free hemoglobin levels) is also pursued, as PT enhances destruction of red blood cells due to increased friction of the unbalanced impeller (11).

Previous studies have suggested the value of log-files analysis of the HeartWare HVAD Ventricular Assist Device (Medtronic Inc., USA) and of early recognition of changes in PPC to resolve the event (16,17). Further, specific patterns of PPC change have been identified and correlated to different "types" of PT (10). Specifically, i) in-pump thrombus build up is accompanied by gradual increase of PPC over time due to progressive deposition of biological material on the surface of the impeller and thrombus growth; ii) suction of a mobilized thrombus leads to abrupt increase of PPC; iii) pre-pump flow obstruction caused by a thrombus occluding the inflow cannula is associated with decrease of PPC, which is typically acute within hours, followed by sudden increase of PPC caused by ingestion of the wedge thrombus into the pump (10,11).

Accordingly, while there is little chance of an early diagnosis of PT due to suction of a mobilized thrombus and sudden—therefore unpredictable—increase in PPC, timely identification of the thrombotic event might be possible in case of in-pump thrombus build up and/or progressive occlusion of the inflow cannula that precedes thrombus ingestion. Nonetheless, the pump thrombus alarm of the HVAD is inherently unable to provide early diagnosis of PT. In the case of in-pump thrombus formation, the alarm is only triggered following high-Watt power spikes (1-2 Watts above the average value), which, however, can not detect the early build up stage of the pump thrombus; indeed, high-Watt power spikes are indicative of major device malfunctioning due to a huge thrombus already formed in the pump. In the case of inflow cannula obstruction, the system does not trigger any alarm of low PPC; in these situations a low flow alarm—intended for the diagnosis of suction events, where the inflow cannula impinges the intraventricular septum—is instead triggered, which, however, requires major decrease of the LVAD flow (approximately 1 to 2 L/min in magnitude).

Kauffman et al. have suggested analysis of the acoustic spectrum of the pump as a means of detecting PT (18). Though, investigation of altered acoustic spectrum (i.e., appearance of third harmonics) is usually performed following first diagnosis of suspected PT, to increase the diagnostic precision and to confirm suspected PT.

As a result, to date no clinical standardized method exists to detect the early phase of PT, preventing the definition of effective therapeutic strategies to limit its progression, clinical manifestation of the event, and associated complications.

Slaughter et al. previously demonstrated the progressive recovery of circadian rhythm in heart failure patients following implantation of a LVAD and suggested that continuous-flow pumps have an intrinsic response to the physiologic circadian rhythmicity of the recipients (19). In their study, the authors described circadian fluctuations in LVAD flow and PPC during normal pump operation, i.e., in patients with no reported adverse clinical events and LVAD parameters within the therapeutic range (19).

Röbesaat J I et al. (Analysis of LVAD log files for the early detection of pump thrombosis. 22nd IEEE Symposium on Computers and Communication (ISCC 2017): Workshops—ICTS4eHealth 2017) described an algorithm for the analysis of circadian variation of PPC as a means of predicting PT in patients implanted with the HeartWare HVAD. The method is based on the analysis of PPC daily variation over time, i.e., time-domain analysis of PPC data, which comprises the calculation of the daily fluctuations of the pump current, the computation of their standard deviation (SD) and the definition of a threshold of pump current increase, defined as SD multiplied by a correcting factor that minimizes false alarms and maximizes true positives. Thus, there is the need for innovative methods to early identify pump dysfunction, in particular associated with the development of a PT to further improve intervention (therapeutic or else) and outcomes.

SUMMARY OF THE INVENTION

The present invention is based on the identification of loss/instability of circadian variation (CV) of the PPC as a reliable marker of the early build up stage of a pump thrombus. Then, early diagnosis of PT via time-frequency analysis of the LVAD log-files prevents its progression and associated life-threatening complications.

In the present invention, a clinically relevant tool for evaluating pump operation during long-term support in patients implanted with the HeartWare HVAD was developed thanks to the identification of a reliable marker for the early diagnosis of PT reflecting major alterations of the patient-pump physiological interplay.

The inventors hypothesized that patients who develop PT due to gradual in-pump thrombus build up or inflow cannula occlusion, might experience instability of circadian rhythmicity of pump operation parameters—namely PPC, due to changes in pump pressure gradient across the pump head that alter the "physiologic" interaction between the pump and the native heart/circulation. Accordingly, the inventors developed a novel method able to detect circadian variation of PPC in LVAD patients, and to evaluate if altered, non-circadian trends of PPC might be identified via log-files analysis. Then, the inventors used this tool to evaluate if loss/instability of PPC CV correlates with the early phase of thrombus formation and might, ultimately, translate into early diagnosis of PT, i.e., into identification of the initial stage of development of the thrombotic event before clinical manifestation of overt pump dysfunctions.

A novel method based on time-frequency analysis of the system log-flies allowing the detection of the intrinsic circadian rhythmicity of the pump power consumption over time is developed.

The inventors evaluated effective restoration of circadian rhythm in 14 patients over the early post-operative period (30-to-60 days of support). Thereafter, data were analyzed in 19 HVAD patients who suffered from pump thrombosis; namely: i) 14 in-pump thrombus build up, and ii) 5 inflow cannula occlusions and later thrombus ingestions were studied.

The inventors demonstrate that: i) HVAD patients effectively gain circadian rhythm following post-operative recovery (93% of the patients, 23±15 days after implantation); ii) long-term stability of circadian variations in patients without complications; iii) severe instability and loss of circadian fluctuations anticipating the thrombotic event, as it was noticed in 89% of the patients 12±6 days before clinical manifestation of overt pump thrombosis (high-Watt power spikes). Furthermore, the invention provides the first clinical evidence of recovery of circadian rhythmicity following non-surgical resolution of the event.

Then, Time-frequency analysis of the HVAD log-files and identification of loss and/or instability of circadian rhythm provides a new tool for early diagnosis of pump dysfunction such as thrombosis, allowing improvement in medical management and decreased need for pump exchange.

The present method is particularly advantageous in that:
it is based on time-frequency analysis, specifically, Wavelet analysis, of the PPC. As a result, the method allows uniquely for identification of the actual frequency component of the PPC associated with its circadian variation (circadian rhythm frequency component, CRFC=$1/24$ h=$1/86400$ s=$1.16e-5$ Hz). Then, early diagnosis of the development of a pump thrombus is pursued via detection of loss/instability of this CRFC;

the present method was proved to be effectively able to discriminate between normal and pathologic frequency content of the PPC, the latter being associated with early development of PT;

the present method allows to capture loss of CRFC of PPC that anticipated two different types of thrombosis: i) gradual build up (n=14, sensitivity=86%), and ii) occlusion of the inflow cannula and subsequent thrombus ingestion by the pump (n=5, sensitivity=100%);

the present method provides outstanding enhanced predictive capability. It predicted the thrombotic event 12±6 days before its clinical manifestation (in Röbesaat et al.: 3±4 days); indeed, the present method does not rely on averaging of multiple circadian cycles thus it allows much earlier detection of abnormalities. The first abnormal circadian cycle is flagged as relevant by the Invention. Indeed, the present method predicts the thrombotic event using an on-off approach, which increases the method reliability: if CRFC is present (i.e., the signal is "on", meaning that the power concentrated around the CRFC of the PPC is >50% of the total signal power), the patient is not at risk of PT, consistent with normal pump operating conditions; on the other side, loss/instability of CRFC (i.e., the signal goes "off") indicates early stage of pump thrombosis, a shown in FIG. 6

Therefore, the present invention provides a method for early detection of an artificial pump dysfunction comprising a time-frequency analysis of the pump motor power consumption (PPC) and the identification of a loss and/or instability of circadian rhythm frequency component (CRFC) of said PPC.

Preferably the artificial pump is a continuous-flow pump for mechanical circulatory support system, preferably a ventricular assist device.

Still preferably the pump dysfunction is caused by a building-up of a thrombus, preferably within the impeller of said pump or is caused by an occlusion, preferably of an inflow cannula of said pump, preferably said pump dysfunction is a pump thrombosis.

Yet preferably the time-frequency analysis of pump motor power consumption (PPC) is performed by Wavelet decomposition of the PPC over time, preferably by real-time Wavelet decomposition of the PPC, preferably by Wavelet decomposition time-frequency analysis, as the magnitude (i.e., power) of the PPC signal in the circadian frequency band ($1/24$ hours±30 min).

More preferably the Wavelet decomposition of the PPC is a Wavelet decomposition with Morlet mother wavelet in the scale range $5 \times 10^{-6}$-$5.5 \times 10^{-4}$ Hz (HVAD sampling frequency: $1.11 \times 10^{-3}$ Hz).

Preferably the time-frequency analysis of pump motor power consumption (PPC) is performed on log-files retrieved from pump controller.

Preferably the loss and/or instability of circadian rhythm frequency component (CRFC) of said PMPC is identified in particular when at a specific time point, power of the signal in the circadian band decreases and is lower than 50% of the total signal power at the same time point subtracted by its Direct Component (DC) and/or is totally absent (power≈0).

The invention also provides a computer-implemented method comprising a time-frequency analysis of pump motor power consumption (PPC) and the identification of a loss and/or instability of circadian rhythm frequency component (CRFC) of said PPC.

The invention also provides a method to prevent low output syndrome, cardiogenic shock, pump thrombus and/or cardiac arrest or death comprising carrying out the method as defined above.

The invention also provides a method to monitor the efficacy of a thrombolytic therapy and/or to optimize intensity and duration of a thrombolytic therapy comprising carrying out the method as defined above.

A thrombolytic therapy may be any thrombolytic therapy known in the art such as anticoagulation and/or fibrinolytics (such as tissue plasminogen activator (tPA), streptokinase (SK), and urokinase (UK), all incorporated by reference).

The invention also provides a computer program product comprising instructions which, when the program is executed by a computer, causes the computer to carry out the methods of the invention.

The invention also provides a computer-readable storage medium having stored thereon the computer program product of the invention.

The invention also provides a data processing apparatus comprising means for carrying out the methods of the invention.

The invention also provides a central processing unit that analyzes time-frequency of pump motor power consumption (PPC) and identifies a loss and/or instability of circadian rhythm frequency component (CRFC) of said PPC.

Preferably the central processing unit is provided with means for generating alarm signals.

The invention also provides an apparatus comprising the central processing unit as defined above.

In the present invention stability of a prevalent CRFC of PPC means that the power of the PPC signal in the circadian frequency band at given time-point is greater than 50% of the total signal power at the same time point subtracted by its Direct Current (DC) component for at least 5 days in a row. Loss of circadian rhythm frequency component (CRFC) of PPC means that the power of the PPC signal in the circadian frequency band approaches 0.

Instability of circadian rhythm frequency component (CRFC) of said PPC means that the power of the PPC signal in the circadian frequency band at a given time-point is lower than 50% of the total signal power at the same time point subtracted by its Direct Current (DC).

The present invention will be illustrated by means of non-limiting examples in reference to the following figures.

FIG. 1: Time-frequency analysis of a representative case showing progressive establishment of circadian rhythmicity of the pump power consumption (PPC) following the device implant (A) The PPC time signal is depicted over 30 consecutive days of support starting from the date of the device implantation (day 0) as retrieved from the HVAD log-files. (B) Left: Wavelet Time-frequency analysis of the PPC: the white arrow indicates establishment of CV, consistent with significant increase of the magnitude (i.e., power) in the circadian frequency band following 16 days of support. Circadian variation maintained stable over time following its appearance (16-to-30 post-operative days), indicating effective establishment of circadian rhythmicity. Right: Fourier analysis of the PPC time signal, demonstrating the establishment of rhythm in the circadian band, consistent with the peak observed at $1.16\pm0.3\times10^{-5}$ Hz.

Figure 2:
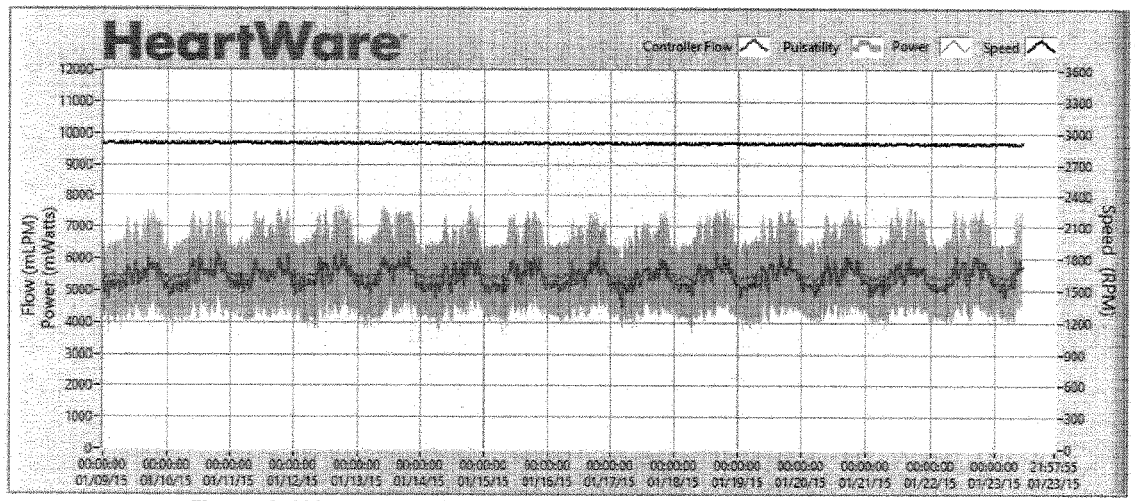
Figure 2:
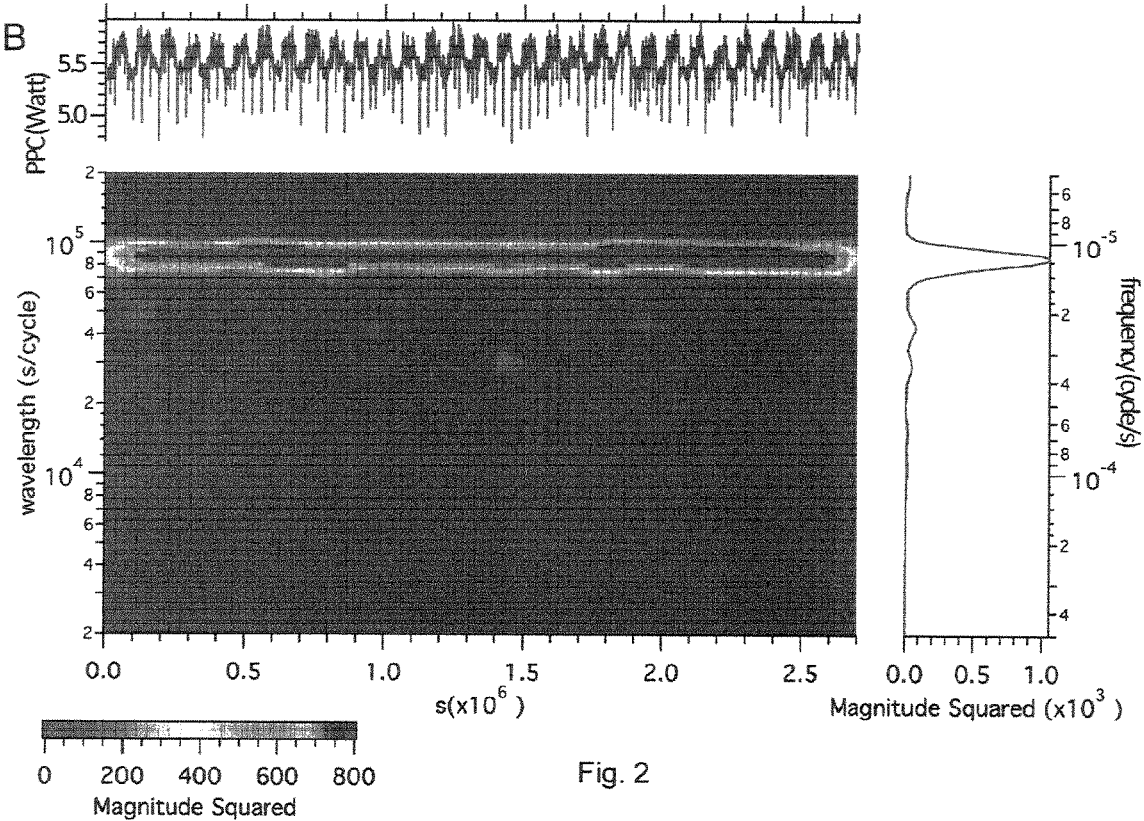

FIG. 2: Representative data of long-term stability of CV of the PPC in patients with no diagnosed adverse events. In the presented case, log files were analyzed following 690 days of support. (A) Log files analysis provided by HeartWare (Medtronic Inc.). (B) Left: Wavelet time-frequency analysis of the PPC: stable CV was observed over 30 days of pump operation, consistent with the recorded magnitude (i.e., power) of the PPC signal in the circadian frequency band. Right: Fourier analysis of the PPC signal demonstrates stability of circadian rhythm, consistent with the peak of power concentration in the $1.16\pm0.3\times10^{-5}$ Hz circadian frequency band.

Figure 3:
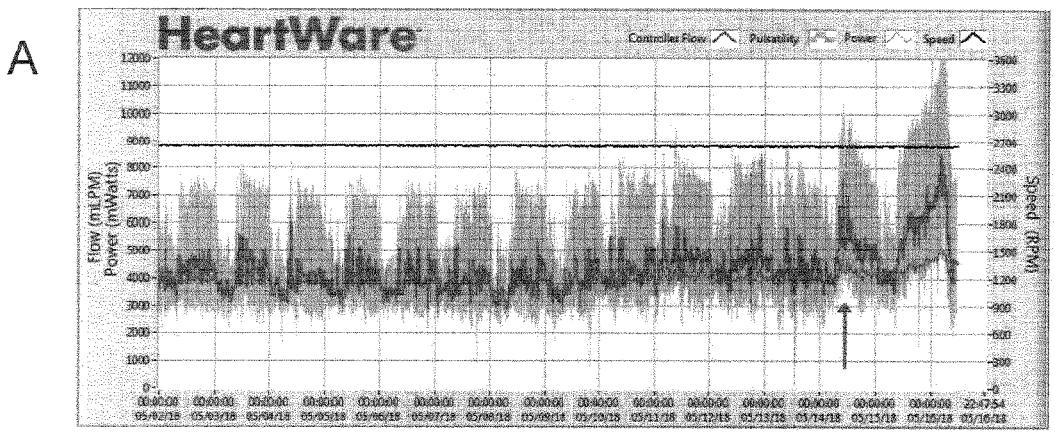
Figure 3:
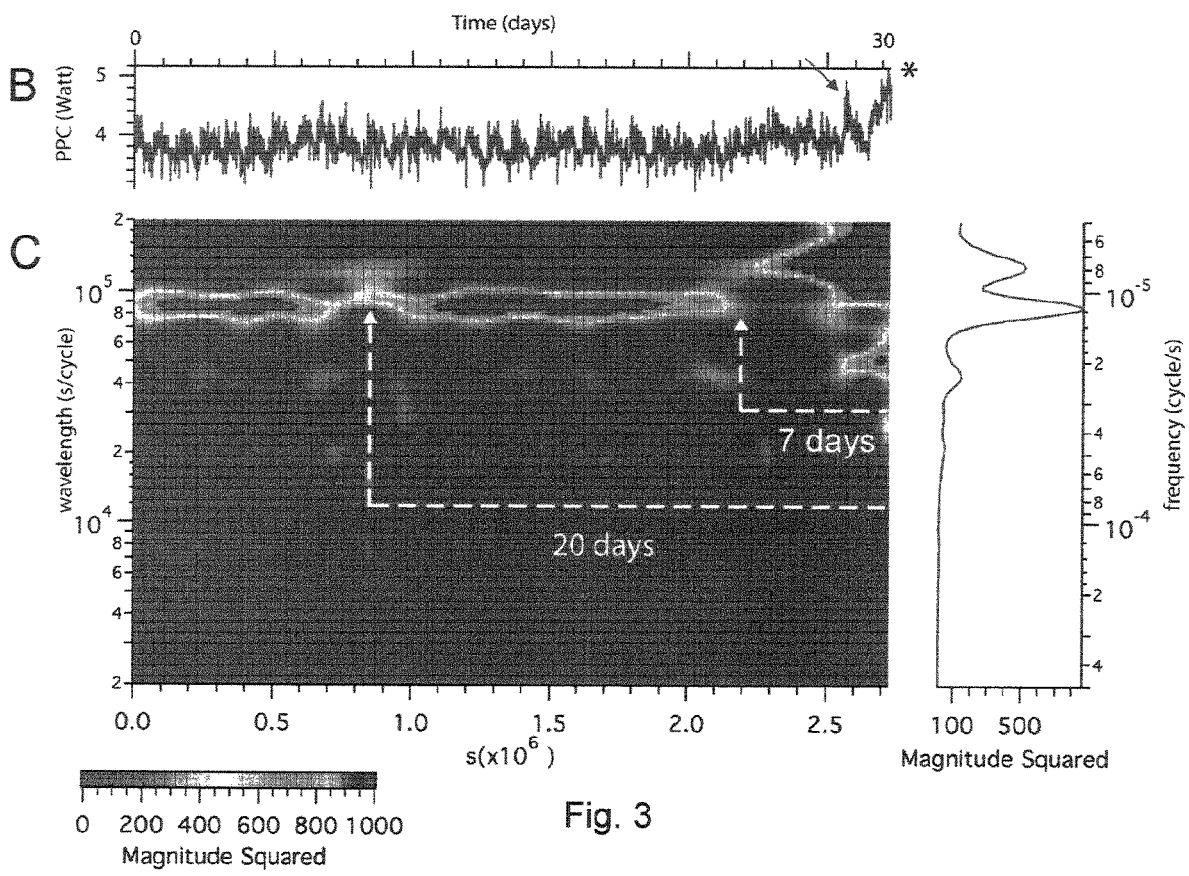

FIG. 3: Representative data showing early loss of circadian variability (CV) of the pump power consumption (PPC) before PT associated with gradual in-pump thrombus build up. (A) Report of log-files analysis provided by HeartWare (Medtronic Inc.) indicates the development of a PT secondary to gradual thrombus build and shows progressive increase of PPC and pump flow over time; the red arrow indicates triggering of the high Watt alarm. (B) PPC time signal over 30 consecutive days of support as retrieved from the HVAD log-files; the red arrow indicates triggering of the high Watt alarm (corresponding to red arrow in A); * indicates clinical manifestation of the thrombotic event (peak of PPC). (C) Left: Wavelet time-frequency analysis of the PPC: the white arrows indicate i) a first instability of circadian rhythmicity of the PPC recorded 20 days before the thrombotic event, consistent with significant decrease of magnitude in the circadian frequency band, and ii) loss of CV recorded 7 days before clinical manifestation of the event. Right: Fourier analysis of the PPC time signal, showing the peak of power concentration in the $1.16\pm0.3\times10^{-5}$ Hz circadian band.

Figure 4:
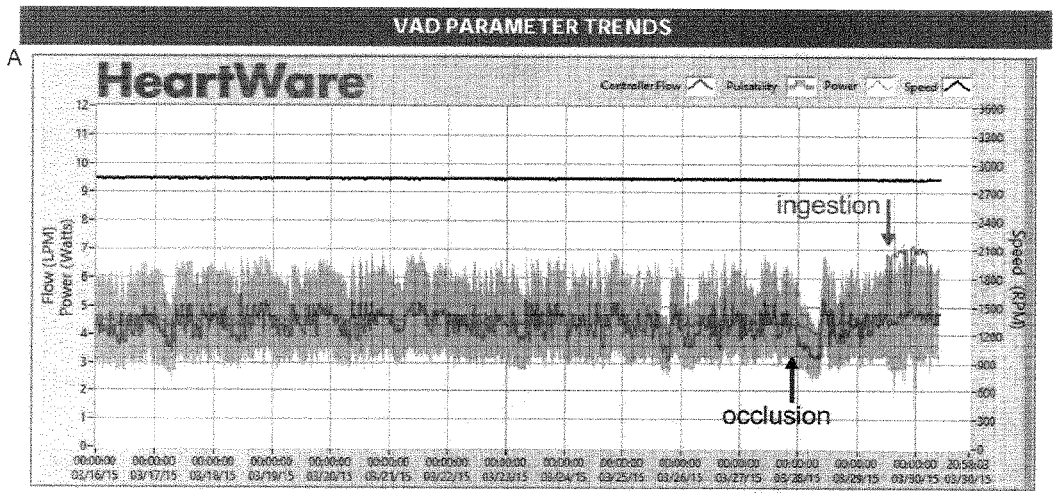
Figure 4:
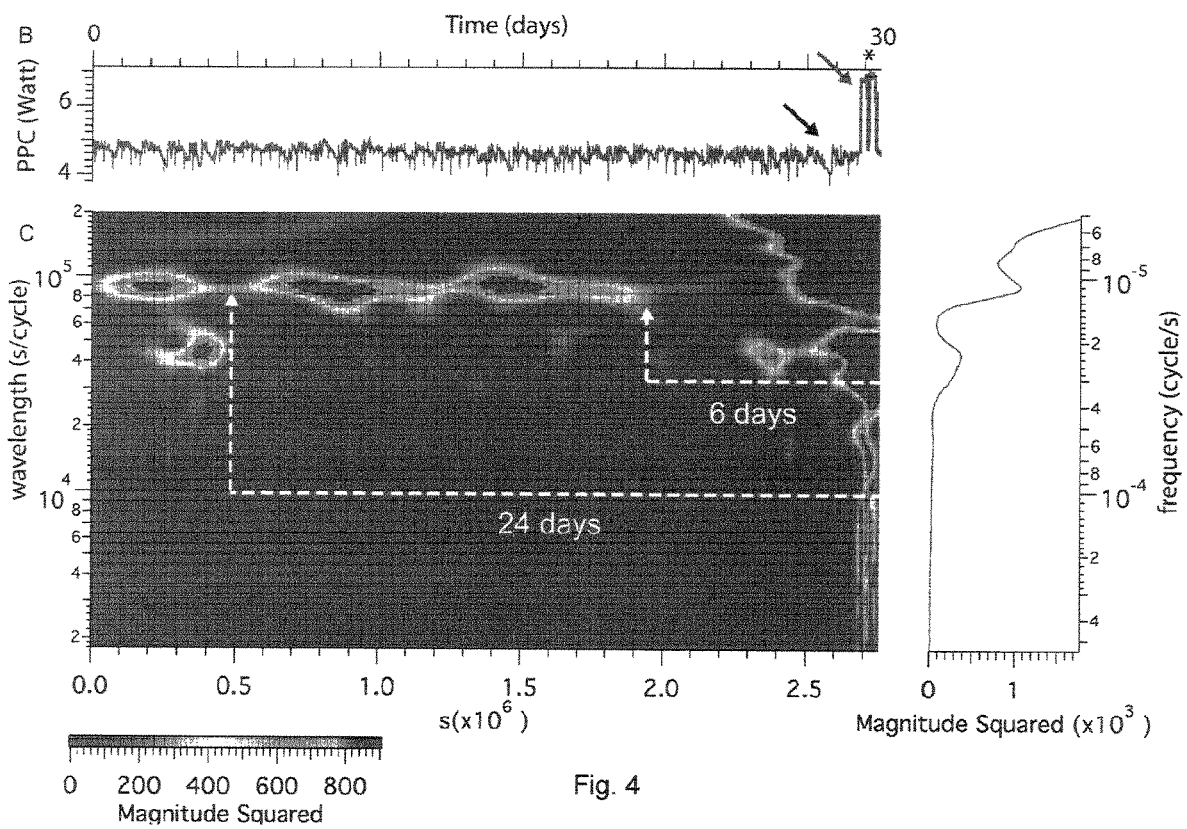

FIG. 4: Representative data showing early loss of circadian variability (CV) of the pump power consumption (PPC) before PT caused by occlusion of the inflow cannula and later thrombus ingestion. (A) Report of log-files analysis provided by HeartWare (Medtronic Inc.) indicates a first significant reduction of PPC and pump flow (black arrow, occlusion) followed by sudden increase in PPC (red arrow, ingestion). (B) PPC time signal over 30 consecutive days of support as retrieved from the HVAD log-files; the black arrow indicates triggering of the HVAD low flow alarm; the red arrow indicates triggering of the high Watt alarm; * indicates clinical manifestation of the thrombotic event (peak of PPC). (C) Left: Wavelet time-frequency analysis of the PPC: the white arrows indicate i) a first instability of circadian rhythmicity of the PPC recorded 24 days before the development of the thrombotic event, consistent with significant decrease of magnitude in the circadian frequency band, and ii) loss of circadian variability recorded 6 days before clinical manifestation of the event. Right: Fourier analysis of the PPC time signal, showing the peak of power concentration in the $1.16\pm0.3\times10^{-5}$ Hz circadian band.

Figure 5:
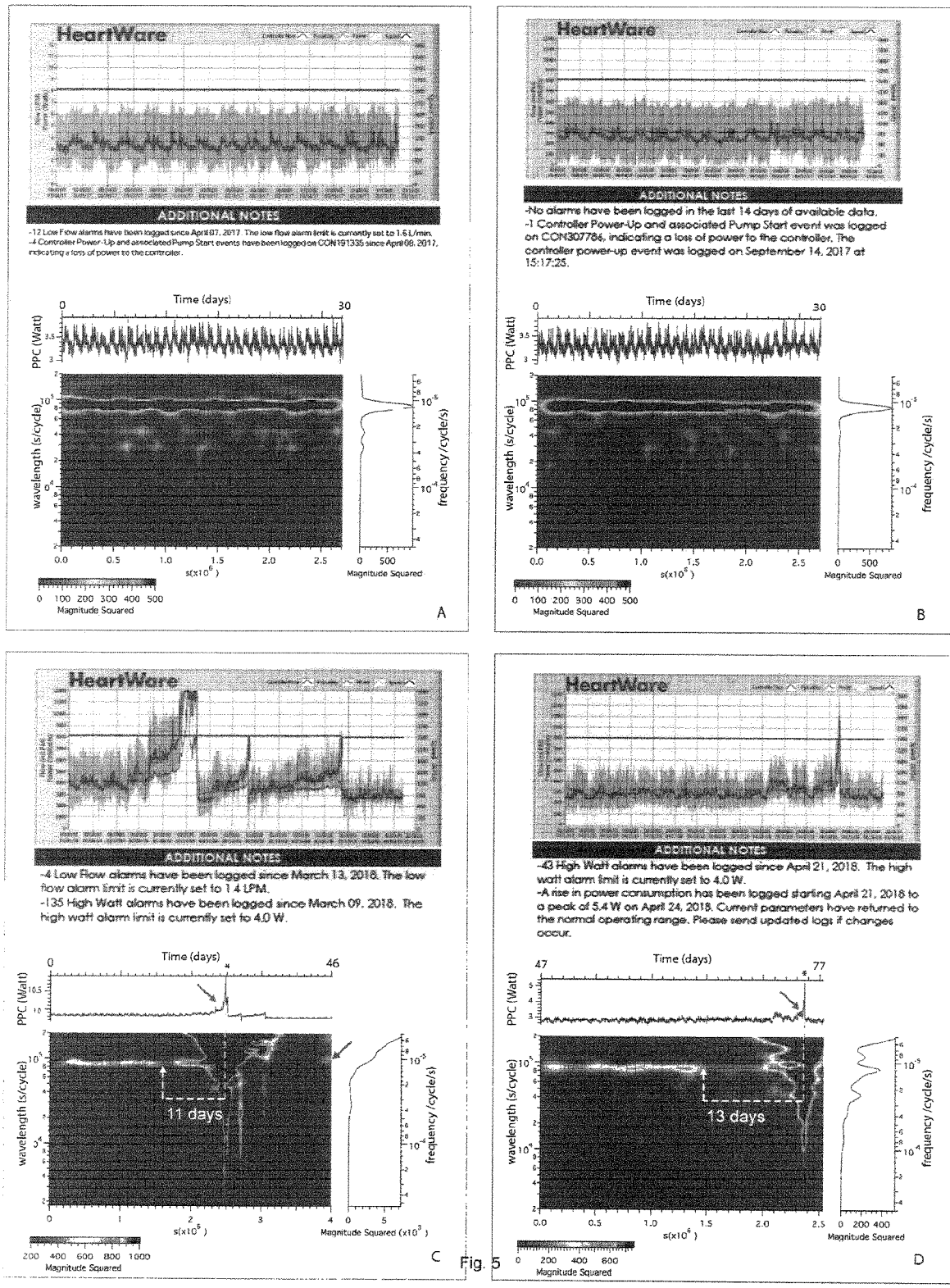

FIG. 5: Analysis of the dynamics of circadian variation (CV) of the pump power consumption (PPC) in a HVAD patient who suffered from recurrent pump thrombosis (PT). Stable CV of the PPC was observed over 30 days of pump operation 12 months (A) and 6 months (B) before the development of the first PT. Loss of CV of the PPC was recorded 11 days before clinical manifestation of the first thrombotic event (C). Recovery of stable CV of the PPC was recorded 18 days following resolution of the event (green arrow in C), which maintained stable until 13 days before the second thrombotic event (D). (C) and (D) depict consecutive time-windows. Red arrows in (C) and (D) indicates triggering of the inbuilt high-Watt alarm of the HVAD. * indicates clinical manifestation of the thrombotic event (peak of PPC).

Figure 6:
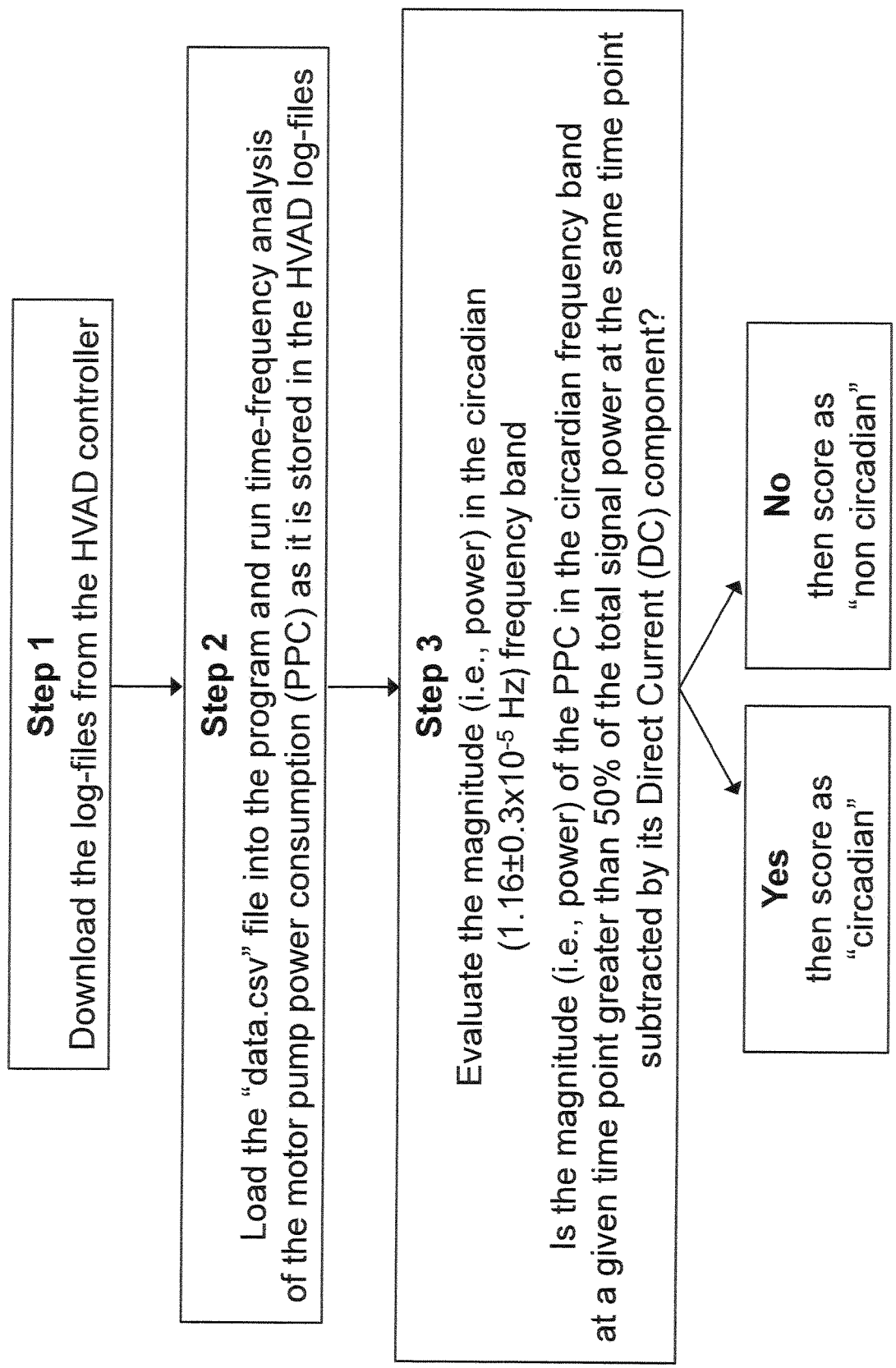

FIG. 6: Schematics of the steps of the method allowing the evaluation of the presence/absence of the circadian rhythm in the motor pump power consumption (PPC).

DETAILED DESCRIPTION OF THE INVENTION

Materials and Methods

Study Design and Patient Population

This study was performed at San Raffaele Scientific Institute in Milan, Italy and was conducted in patients implanted with the HeartWare HVAD Ventricular Assist Device (Medtronic Inc., USA). The HVAD system consists of an implantable centrifugal-flow pump connected to an external controller (20). The controller of the HVAD allows uniquely for downloading and post-processing of the log-files, where PPC, whose actual value is Iteratively recorded every 15 minutes, is stored over 30 consecutive days of pump operation.

All data (log-files) analyzed in this study were provided by Medtronic Inc.

First, the inventors retrospectively analyzed log-files of HVAD patients with sinus rhythm and stable clinical conditions in the early post-operative period (i.e., the first 30-to-60 days of support) to verify that the present tool was able to identify restoration of circadian rhythm (19).

This set of data represents the baseline cohort, meaning that it was used to define a suitable setting of the parameters of the inventors' method to detect CV of the PPC.

Second, the inventors retrospectively analyzed log files of patients with no reported events of PT in the long-term to evaluate effective stability of circadian rhythmicity.

Then, the inventors retrospectively analyzed log-files of HVAD patients who suffered from PT. Log-files that preceded clinical manifestation of the thrombotic event were analyzed over 30 days. The aim of the analysis was to: i) test the reliability and robustness of the inventors' method as for detection of CV of PPC before the event occurrence (validation cohort); and, ii) identify alterations of CV of the PPC associated with early pump operating dysfunctions, i.e., with the initial stage of PT, before its clinical manifestation. For each patient, the time at which the method recorded a significant alteration of CV of the PPC was recorded and the prognostic power of the inventors' method was compared vs. the standard HVAD high-Watt alarm system.

Time-Frequency Analysis of Circadian Variation of Pump Power Consumption

Log-files were downloaded from the HVAD controller and time-frequency analysis was performed to highlight the presence of repetitive circadian variations (CV) of the PPC signal over time. Time-frequency analysis allows detecting the presence of different frequency components in a time series, at single time points, as well as over their temporal evolution. Accordingly, time-frequency analysis allowed quantifying the presence of the frequency of Interest over the 30 days log-file time-series, that is the frequency component associated with daily circadian rhythmicity of the PPC. CV was identified consistent with the power (i.e., the magnitude) of the PPC signal within the circadian frequency band ($1.16 \pm 0.3 \times 10^{-5}$ Hz, corresponding to $\frac{1}{24}$ hours $\pm 30$ minutes).

The inventors performed Time-frequency analysis of the PPC signal via custom made and in-built IgorPro6 (Wavemetrics®) procedures; in particular, the inventors employed Wavelet decomposition with Morlet mother wavelet (21) in the scale range $5 \times 10^{-6}$-$5.5 \times 10^{-4}$ Hz (HVAD sampling frequency: $1.11 \times 10^{-3}$ Hz). In this procedure, the inventors measured power in the frequency band associated with CV. CV was defined as prevalent at a specific time point if power in the circadian band was greater than 50% of the total signal power at the same time point subtracted by its DC component; CV was defined as stable, if it remained prevalent for at least 5 days in a row.

Statistical Analysis

Data are presented as mean with standard deviation (SD). Normality of the distribution was assessed via the Shapiro-Wilk test. The Student's t-test was used to evaluate differences between groups. A p-value <0.05 was assumed as statistically significant.

EXAMPLES

Example 1. Analysis of Recovery of Circadian Rhythmicity in the Early Post-Operative Period Fourteen patients with available data in the first 30/60 post-operative days time-window met the inclusion criteria and log-files of these patients were analyzed.

The inventors' method demonstrated optimal clinical competency for detection of CV of the PPC; indeed, the inventors observed effective restoration of CV of the PPC in 13 out of 14 (93%) patients following $23 \pm 15$ days of HVAD support. Restoration of CV was consistent with significant increase of the magnitude (i.e., power) of the PPC signal in the circadian frequency band. Representative data are shown in FIG. 1. In the presented case, while CV of the PPC signal was strongly unstable or totally absent (magnitude=0, red colored in FIG. 1) over the first 15 days of support, the power in the circadian band increased significantly starting from day 16 (magnitude >0; FIG. 1). Furthermore, circadian rhythmicity remained stable following its appearance over the whole analyzed time-window (no instability/decrease of power/loss of CV were observed), indicating effective establishment of optimized pump operating conditions.

Example 2. Analysis of Long-Term Circadian Rhythmicity in Patients with No Diagnosed Adverse Events Log files of 12 patients with no reported thrombotic adverse events were provided and analyzed. Median time of support was 962 (445-1447) days. The inventors observed long-term stability of CV of the PPC in 11 out of 12 (92%) patients, consistent with the measured magnitude (i.e., power) of the PPC in the circadian frequency band (FIG. 2). Pronounced instability of CV was recorded in 1 patient with severe right ventricular dysfunction. In addition, the data suggest that variation of the pump speed dictated by clinical needs is unlike to induce disruption of CV as it was observed in one patient in this cohort and further corroborate the reliability of the tool to recognize variations of circadian rhythmicity associated with clinical events.

Example 3. Analysis of Circadian Rhythmicity in Patients with PT

Log-files of 19 thrombotic events were analyzed, specifically, 14 in-pump gradual build up and 5 thrombus ingestions secondary to inflow cannula occlusion.

The inventors observed loss of CV of the PPC in 17 out of 19 patients (89%) who suffered from PT $12 \pm 6$ days before clinical manifestation of the thrombotic event (Table 1).

TABLE 1

Loss of circadian variability (CV) of the pump power consumption (PPC) in patients with clinically diagnosed pump thrombosis (PT)

| | All PTs | Build up PT | Thrombus Ingestion |
|---|---|---|---|
| Number of events | 19 | 14 | 5 |
| Loss of CV as detected by time-frequency analysis of the log-files | 17 (89%) | 12 (86%) | 5 (100%) |
| Time of loss of CV (days before the thrombotic event as diagnosed by the HVAD high Watt alarm) | 12 ± 6 | 12 ± 7 | 11 ± 5 |
| Time of triggering of the PT high-Watt alarm of the HVAD (days before the thrombotic event) | 1.6 ± 1.7 | 1.8 ± 1.8 | 1.2 ± 1.6 |

Comparison of the predictive power of the inventors' method (detection of loss of CV) vs. inbuilt standard HVAD alarm (detection of high Watts) Indicates that the inventors' method was characterized by enhanced prognostic capability and associated significant improvement of early diagnosis (time-frequency analysis: 12±6 days vs. Inbuilt HVAD alarm: 1.6±1.7 days, p<0.0001).

In particular, in the case of build-up PTs, the method detected loss of CV in 12 out of 14 patients (86%) 12±7 days before clinical manifestation of the event (Table 1; p<0.0001 vs. HVAD alarm); in the case of thrombus ingestion, the method detected loss of CV in all of the 5 events (100%) 11±5 days before clinically overt PT (Table 1; p=0.008 vs. HVAD alarm). Clinical manifestation of PT was identified from log-files data analysis as the date at which the peak of PPC was reached. Representative data of build-up PT and thrombus ingestion are shown in FIGS. 3 and 4, respectively. Loss of CV was consistent with sudden decrease of the magnitude (i.e., power) in the circadian frequency band of the PPC signal. In the presented cases, power in the circadian frequency band progressively decreased until being completely absent 7 days before clinical manifestation of the build up PT event (FIG. 3) and 6 days before thrombus ingestion (FIG. 4), respectively. In both cases a first significant instability of PPC circadian rhythmicity was recorded 20 (FIG. 3) and 24 (FIG. 4) days before overt pump thrombosis, respectively.

Results of the analysis of CV of the PPC performed in a patient who suffered from recurrent PT (n=2 in-pump build up thrombus) are shown in FIG. 5, further enlightening the robustness and reliability of the inventors' method for early detection of loss of CV and early diagnosis of PT. In the presented case, the inventors observed the presence of stable CV of the PPC over two different 30-days log-files time-windows analyzed i) 12 months (FIG. 5A) and ii) 6 months (FIG. 5B) ahead the first thrombotic event. Conversely, loss of CV was detected 11 days before clinical manifestation of a first PT (FIG. 5C). Further, the inventors' data indicate restoration of CV following resolution of the first event (18 days after the event, FIG. 5D). Afterward, loss of CV was again detected, which anticipated a second thrombotic event: in this case, the inventors' method predicted the thrombotic event 13 days before its clinical manifestation (FIG. 5D).

The present invention describes a novel tool for the evaluation of HVAD pump operations during long-term support and highlights its value for the early identification of major complications, namely pump thrombosis (PT). The tool is based on the analysis of the system log-files. Specifically, the method the inventors developed allows characterizing the presence (or absence) of intrinsic circadian variation (CV) of the pump power consumption (PPC) in HVAD patients. Indeed, the inventors show that HVAD patients gain circadian rhythm following post-operative recovery (FIG. 1). Circadian rhythmicity consists of reproducible changes of PPC and flow over daytime and is detected by the inventors' method via Wavelet decomposition time-frequency analysis, as the magnitude of the PPC signal in the circadian frequency band ($\frac{1}{24}$ hours±30 min). This phenomenon can be explained by physiological interaction between the native heart, the HVAD pump, and the systemic circulation, confirming the strong interplay between continuous-flow pumps and the patient's cardiovascular system.

As these interactions require unobstructed blood flow through the pump, the inventors supposed that early thrombus formation might produce abnormal changes of the PPC before clinical evidence or triggering of the alarm controller. As such, the potential to discriminate between physiologic (normal pump operating conditions) and pathologic (non-circadian) patterns of the PPC signal might turn into a clinically relevant tool for early Identification of PT and thromboembolic events.

The present invention is consistent with previous data, where the different patterns of PPC changes during all scenarios of thrombotic obstructions of blood flow through the HVAD have been characterized (10,15,17). Those data provided validation of the inventors' method. However, though recognized as a valuable diagnostic tool at the time of the clinical event, currently used method of data analysis does not have the acuity to trigger medical interventions before overt thrombosis. Indeed, analysis of PPC changes over time and identification of high-Watt power spikes intrinsically limits the predictive capability, as the recognition of frequency oscillations of the PPC baseline is prevented. Further refinements of this approach are unlikely to increase early sensitivity upon thrombotic events: lowering the threshold for high-Watt spikes i) would trigger false alarms as a function of (low) power peaks that follow physiological circadian oscillation of PPC, ii) would negatively affect patients quality of life because of recurring false alarms, and iii) lastly, might trigger unnecessary medical interventions.

Conversely, the inventors' approach moves standard analysis of the temporal evolution of the PPC towards the evaluation of its intrinsic circadian variability in the frequency domain, thus providing a breakthrough shift with respect to the state-of-the-art paradigm for the diagnosis of PT. Time-frequency analysis and identification of CV does not look at power spikes; conversely, the analysis is based on the recognition of intrinsic fluctuations of the frequency content of the PPC baseline. Time-frequency analysis is performed on log-files retrieved from the HVAD controller, where PPC values are recorded iteratively every 15 minutes. As such, PPC values corresponding to the Lavare cycle might be randomly stored in the time-series. However, being characterized by much higher frequency components, this is highly unlikely to significantly influence recognition of CV pattern.

Time-frequency analysis of the PPC achieved unprecedented early sensitivity to abnormal pump operating dysfunctions, which correlate with the initial stage of the thrombotic event (Table 1). The inventors' approach allows not only characterizing the presence of CV at single time points (i.e., single days of support), but also the presence of repetitive CV over time (i.e., over consecutive days of support). Thanks to these peculiar characteristics, time-frequency analysis allowed quantifying i) the recovery of CV following the device implantation and post-operative recovery (FIG. 1), ii) stability of CV over time in patients with no reported adverse clinical events (FIG. 2), iii) alteration of CV that anticipates clinical manifestation of a thrombotic event (FIG. 3,4), and iv) recovery of CV following the event resolution (FIG. 5). Importantly, among the patterns of blood flow obstruction through the pump, the inventors' method is able to identify early not only thrombus build up within the impeller (sensitivity: 86%, 12 days before on average; Table 1), but also occlusions of the inflow cannula that precedes later thrombus ingestion, with apparent superior predictive capability (sensitivity: 100%, 11 days before on average; Table 1).

Then, the inventors developed new diagnostic tool to be integrated on board of the HVAD external controller. In detail, the method might be embedded within a miniaturized central processing unit (CPU) allowing real-time Wavelet decomposition of the PPC and equipped with ad-hoc alarm signals driven by the method output data. Such a system might anticipate recognition of major thrombotic complications, thus reducing their progression, associated morbidity, as well as attendant costs related to its treatment, facilitating prompt diagnosis and medical management. Early detection of thrombotic complications might immediately translate into earlier readmission, earlier treatment, and, as such, higher success of medical therapy. Indeed, the inventors know from literature that success of any non-surgical treatment of PT (IV heparin/thrombolytics) is strongly dependent from the time of event recognition (10,16,17). In particular, the alarm appropriately triggers patients' evaluation and eventually assessment of the coagulation profile and guide prompt initiation of inherent therapies aimed at resolving the event. Of note, avoidance of unnecessary pump exchange would have tremendous clinical value, lowering complications and attendant costs. The inventors emphasize that the value of any technological improvement of LVAD support envisioned in the perspective of acceptable patient's quality of life might not be underestimated. In this perspective, this miniaturized CPU system for analysis of circadian rhythmicity will not increase the weight and dimensions of the system, nor worsen wearability of the bag that holds the controller.

Further, the present method optimizes intensity and duration of thrombolytic therapy to reduce drug-related side-effects (bleeding) associated with unnecessary drug administration: indeed, inventors' approach allows detecting recovery of CV following initiation of lytics (FIG. 5) that the inventors hypothesized to be indicative of event resolution associated with restoration of optimal pump operation. The present method is applicable to any LVAD systems (even centrifugal or axial pumps), such as the HeartMate3 (Abbott Laboratories, USA) or newly emerging VADs, as well as other clinical settings, e.g., temporary short-term mechanical circulatory support systems, such as the Impella® (Abiomed Inc., USA), which is characterized by high prevalence of complications, both thrombotic and hemorrhagic. In addition, although LVAD systems with reduced thrombogenicity are now commercially available, these are not free from thromboembolic events (namely stroke) (3). These events are often triggered by propulsion of in-pump thrombi downstream of the pump itself. In particular, increased clearance gap between the housing and the blades of the HeartMate3 LVAD (Abbot Laboratories, USA) (22) facilitates expulsion of small thrombi adhered on the surface of the impeller or ingested from the inflow cannula before their growth and major impairment of pump operation. Furthermore, with increased clearance gap, the presence of small thrombi might not significantly impair friction of the rotating impeller. Accordingly, high-Watt power spikes that might advise of early thrombosis are not triggered and these phenomena remain unnoticed and might evolve towards clinically relevant adverse events. The present method may also be used for such LVAD systems as, as shown here major alterations of CV of PMPC are Identified earlier than the formation of huge thrombi and associated high-Watt power spikes.

In conclusion, the inventors developed a new tool based on time-frequency analysis of the HVAD log-files to characterize pump operation during long-term support and to early identify major complications, namely pump thrombosis. The inventors' tool has effective clinical translation to improve the results of non-surgical treatment of adverse thrombotic events. The inventors demonstrated, for the first time, that: i) HVAD patients develop circadian rhythmicity following post-operative recovery; ii) circadian rhythmicity remains stable in the long-term in patients with no recorded thrombotic complications and LVAD parameters within the therapeutic range; iii) the early stage of pump thrombosis alters the Intrinsic circadian variability of the pump power consumption, which enhances the potential to early identify the thrombotic event before its clinical manifestation; iv) resolution of the thrombotic event is accompanied by recovery of stable circadian variability of the power consumption. With this tool the inventors achieved unprecedented enhanced predictive capability of thrombotic complications with respect to current HVAD diagnostic system of pump thrombosis, which is limited by its intrinsic inability to look at frequency oscillations of the power consumption over time and does not have any potential to trigger medical interventions before overt thrombosis. This study also shows the value of systematic monitoring of circadian rhythm in HVAD patients to provide a comprehensive clinical and technical evaluation of the patient status, pump operation, and their physiological interplay. Avoidance of unnecessary pump exchange surgery would have tremendous clinical value, lowering complications and attendant costs associated with its treatment.

BIBLIOGRAPHIC REFERENCES

1. Slaughter M S, Rogers J G, Milano C A, Russell S D, Conte J V, Feldman D, Sun B, Tatooles A J, Delgado R M 3rd, Long J W, Wozniak T C, Ghumman W, Farrar D J, Frazier O H; HeartMate II Investigators. Advanced heart failure treated with continuous-flow left ventricular assist device. N Engl J Med 2009; 361:2241-51.
2. Rogers J G, Pagani F D, Tatooles A J, Bhat G, Slaughter M S, Birks E J, Boyce S W, Najar S S, Jeevanandam V, Anderson A S, Gregoric I D, Mallidi H, Leadley K, Aaronson K D, Frazier O H, Milano C A. Intrapericardial Left Ventricular Assist Device for Advanced Heart Failure. N Engl J Med. 2017; 376(5):451-460.
3. Mehra M R, Naka Y, Uriel N, Goldstein D J, Cleveland J C Jr, Colombo P C, Walsh M N, Milano C A, Patel C B, Jorde U P, Pagani F D, Aaronson K D, Dean D A, McCants K, Itoh A, Ewald G A, Horstmanshof D, Long J W, Salemo C; MOMENTUM 3 Investigators. A Fully Magnetically Levitated Circulatory Pump for Advanced Heart Failure. N Engl J Med. 2017; 376(5):440-450.
4. Kirklin J K, Naftel D C, Pagani F D, Kormos R L, Myers S, Acker M A, Rogers J, Slaughter M S, Stevenson L W. Pump thrombosis in the Thoratec HeartMate II device: An update analysis of the INTERMACS Registry. J Heart Lung Transplant. 2015; 34(12):1515-26.
5. Mehra M R, Stewart G C, Uber P A. The vexing problem of thrombosis in long-term mechanical circulatory support. J Heart Lung Transplant. 2014; 33(1):1-11.
6. Najar S S, Slaughter M S, Pagani F D, Starling R C, McGee E C, Eckman P, Tatooles A J, Moazami N, Kormos R L, Hathaway D R, Najarian K B, Bhat G, Aaronson K D, Boyce S W; HVAD Bridge to Transplant ADVANCE Trial Investigators. An analysis of pump thrombus events in patients in the HeartWare ADVANCE bridge to transplant and continued access protocol trial. J Heart Lung Transplant. 2014; 33(1):23-34.
7. de Blasi A R, Manning K B, Saleml A. Science for surgeons: understanding pump thrombogenesis in continuous-flow left ventricular assist devices. J Thorac Cardiovasc Surg. 2015; 149(3):667-73.
8. Consolo F, Pozzi L, Sferrazza G, Della Valle P, D'Angelo A, Slepian M J, Pappalardo F. Which Antiplatelet Therapy in Patients With Left Ventricular Assist Device and Aspirin Allergy? Ann Thorac Surg. 2018 February; 105(2): e47-e49.
9. Consolo F, Sferrazza G, Motolone G, Contri R, Valerio L, Lembo R, Pozzi L, Della Valle P, De Bonis M, Zangrillo A, Fiore G B, Redaelli A, Slepian M J, Pappalardo F. Platelet activation is a preoperative risk factor for the development of thromboembolic complications in patients with continuous-flow left ventricular assist device. Eur J Heart Fail. 2018; 20(4):792-800.
10. Jorde U P, Aaronson K D, Najjar S S, Pagani F D, Hayward C, Zimpfer D, Schlöglhofer T, Pham D T, Goldstein D J, Leadley K, Chow M J, Brown M C, Uriel N. Identification and Management of Pump Thrombus in the HeartWare Left Ventricular Assist Device System: A Novel Approach Using Log File Analysis. JACC Heart Fail. 2015; 3(11):849-56.
11. Scandroglio A M, Kaufmann F, Pied M, Kretzschmar A, Müller M, Pergantis P, Dreysse S, Falk V, Krabatsch T, Potapov E V. Diagnosis and Treatment Algorithm for Blood Flow Obstructions in Patients With Left Ventricular Assist Device. J Am Coll Cardiol. 2016; 67(23):2758-2768.
12. Dang G, Eppera N, Muppidi V, Sahr N, Pan A, Simpson P, Baumann Kreuziger L. Medical Management of Pump-Related Thrombosis in Patients with Continuous-Flow Left Ventricular Assist Devices: A Systematic Review and Meta-Analysis. ASAIO J. 2017; 63(4):373-385.
13. Kirklin J K, Naftel D C, Pagani F D, Kormos R L, Stevenson L W, Blume E D, Myers S L, Miller M A, Baldwin J T, Young J B. Seventh INTERMACS annual report: 15,000 patients and counting. J Heart Lung Transplant 2015; 34:1495-504.
14. Baras Shreibati J, Goldhaber-Fiebert J D, Banerjee D, Owens D K, Hlatky M A. Cost-Effectiveness of Left Ventricular Assist Devices in Ambulatory Patients With Advanced Heart Failure. JACC Heart Fall. 2017; 5(2): 110-119.
15. Chorpenning K, Brown M C, Voskoboynikov N, Reyes C, Dleram A E, Tamez D. HeartWare controller logs a diagnostic tool and clinical management aid for the HVAD pump. ASAIO J. 2014; 60(1):115-8.
16. Kamouh A, John R, Eckman P. Successful treatment of early thrombosis of HeartWare left ventricular assist device with intraventricular thrombolytics. Ann Thorac Surg. 2012; 94(1):281-3.
17. Santise G, Sciacca S, Baglini R, Clemenza F, Pilato M. Can learning to interpret pump messages help lead to an early diagnosis of HeartWare ventricular assist device thrombosis? ASAIO J. 2012; 58(6):629-32.
18. Kaufmann F, Hörmandinger C, Stepanenko A, Kretzschmar A, Soltani S, Krabatsch T, Potapov E, Hetzer R. Acoustic spectral analysis for determining pump thrombosis in rotary blood pumps. ASAIO J. 2014; 60(5): 502-7.
19. Slaughter M S, ising M S, Tamez D, O'Driscoll G, Voskoboynikov N, Bartoli C R, Koenig S C, Giridharan G A. Increase in circadian variation after continuous-flow ventricular assist device implantation. J Heart Lung Transplant. 2010; 29(6):695-7.
20. Larose J A, Tamez D, Ashenuga M, Reyes C. Design concepts and principle of operation of the HeartWare ventricular assist system. ASAIO J. 2010; 56(4):285-9.
21. Chui C K. An Introduction to Wavelets, Volume 1 (Wavelet Analysis and Its Applications) 1st Edition. ISBN: 0121745848. Academic Press (1992).
22. Bourque K, Cotter C, Dague C, Harjes D, Dur O, Duhamel J, Spink K, Walsh K, Burke E. Design Rationale and Preclinical Evaluation of the HeartMate 3 Left Ventricular Assist System for Hemocompatibility. ASAIO J. 2016; 62(4):375-83.

The invention claimed is:

1. A method for early detection of an artificial pump dysfunction comprising:
  a time-frequency analysis of the pump motor power consumption (PPC) using Morlet Wavelet decomposition analysis; and
  identifying a loss and/or instability of circadian rhythm frequency component (CRFC) of said PPC based on a magnitude of the loss and/or instability of the CRFC whereby the early detection of artificial pump dysfunction is accomplished prior to clinical manifestation of said pump dysfunction.

2. The method of claim 1 wherein the artificial pump is a continuous-flow pump for mechanical circulatory support.

3. The method of claim 2, wherein the artificial pump is a ventricular assist device.

4. The method of claim 1 wherein the pump dysfunction is caused by a building-up of a thrombus in any region of the pump.

5. The method of claim 4, wherein the building-up of a thrombus is within the impeller of said pump, or caused by an occlusion of an inflow or outflow cannula of said pump.

6. The method of claim 1 wherein the Morlet Wavelet decomposition analysis of the PPC is performed in the scale range $5 \times 10^{-6}$-$5.5 \times 10^{-4}$ Hz (HVAD sampling frequency: $1.11 \times 10^{-3}$ Hz).

7. The method of claim 1 wherein the time-frequency analysis of pump motor power consumption (PPC) is performed on log-files retrieved from pump controller.

8. The method of claim 1 wherein the magnitude of the loss and/or instability of circadian rhythm frequency component (CRFC) of said PPC is identified when at a specific time point, power of the signal in the circadian band decreases and is lower than 50% of the total signal power at the same time point subtracted by its Direct Component (DC) and/or is totally absent (power≈0).

9. A computer-implemented method comprising a time-frequency analysis of pump motor power consumption (PPC) and the identification of a loss and/or instability of circadian rhythm frequency component (CRFC) of said PPC as defined in claim 1.

10. A computer program product comprising instructions which, when the program is executed by a computer, causes the computer to carry out the method of claim 9.

11. A computer-readable storage medium having stored thereon the computer program product of claim 10.

12. A data processing apparatus comprising means for carrying out the method of claim 9.

13. A method to prevent low output syndrome, cardiogenic shock, pump thrombus and/or cardiac arrest or death comprising carrying out the method as defined in claim 1.

14. A method to monitor the efficacy of a thrombolytic therapy and/or to optimize intensity and duration of a thrombolytic therapy comprising carrying out the method as defined in claim 1.

15. A central processing unit configured to analyze time-frequency of pump motor power consumption (PPC) and configured to identify a loss and/or instability of circadian rhythm frequency component (CRFC) of said PPC as defined in claim 1.

16. The central processing unit of claim 15, wherein central processing unit is further configured to generate alarm signals.

17. An apparatus comprising the central processing unit as defined in claim 15.

18. The method of claim 1, wherein the Morlet Wavelet decomposition analysis of the PPC over time is real-time Morlet Wavelet decomposition analysis of the PPC.

19. The method of claim 18, wherein the real-time Morlet Wavelet decomposition analysis of the PPC is by Morlet Wavelet decomposition time-frequency analysis, as the magnitude of the PPC signal in the circadian frequency band ($1/24$ hours±30 min).

\* \* \* \* \*